United States Patent
Trusgnich

(10) Patent No.: US 9,504,714 B2
(45) Date of Patent: Nov. 29, 2016

(54) METHOD FOR TREATING BLOOD PLASMA INCLUDING A STEP OF WASHING BY MEANS OF DISPERSION

(75) Inventor: Thierry Trusgnich, Sucy en Brie (FR)

(73) Assignee: LFB Biomedicaments, Les Ulis (FR)

( * ) Notice: Subject to any disclaimer, the term of this patent is extended or adjusted under 35 U.S.C. 154(b) by 613 days.

(21) Appl. No.: 13/510,553

(22) PCT Filed: Nov. 18, 2010

(86) PCT No.: PCT/IB2010/055263
§ 371 (c)(1),
(2), (4) Date: Jul. 24, 2012

(87) PCT Pub. No.: WO2011/061705
PCT Pub. Date: May 26, 2011

(65) Prior Publication Data
US 2013/0140237 A1    Jun. 6, 2013

(30) Foreign Application Priority Data

Nov. 18, 2009   (FR) ...................... 09 58145

(51) Int. Cl.
| | | |
|---|---|---|
| A61K 35/16 | (2015.01) | |
| C07K 1/36 | (2006.01) | |
| B01F 3/00 | (2006.01) | |
| B01F 7/00 | (2006.01) | |
| A61M 1/36 | (2006.01) | |

(52) U.S. Cl.
CPC ............... *A61K 35/16* (2013.01); *C07K 1/36* (2013.01); *A61M 1/36* (2013.01); *B01F 3/00* (2013.01); *B01F 7/008* (2013.01); *Y10S 530/83* (2013.01); *Y10S 530/831* (2013.01)

(58) Field of Classification Search
CPC ........... A61K 35/16; C07K 1/36; B01F 3/00; B01F 7/008; Y10S 530/83; Y10S 530/831; A61M 1/36
USPC ....... 210/253, 255, 257, 256, 380, 782, 494, 210/710; 530/381, 382, 383, 384; 424/94.64
See application file for complete search history.

(56) References Cited

U.S. PATENT DOCUMENTS

| | | | | |
|---|---|---|---|---|
| 4,791,191 A | * | 12/1988 | Hao .............................. | 530/362 |
| 7,297,261 B2 | * | 11/2007 | Bomberger et al. .......... | 210/252 |
| 2001/0036125 A1 | * | 11/2001 | Bachelier ............ | B01F 7/00866 366/294 |
| 2004/0029164 A1 | * | 2/2004 | Ransohoff ................ | C07K 1/30 435/6.16 |
| 2008/0207878 A1 | * | 8/2008 | Michel et al. ................ | 530/414 |

\* cited by examiner

*Primary Examiner* — Krishnan S Menon
*Assistant Examiner* — Waqaas Ali
(74) *Attorney, Agent, or Firm* — IP Attorneys Group, LLC

(57) ABSTRACT

The present invention relates to a method for treating blood plasma including the steps of ethanol precipitation of the plasma or a fraction of plasma, recovering the precipitate, washing said precipitate, recovering a washed plasma paste, and making said washed plasma paste soluble.

11 Claims, 1 Drawing Sheet

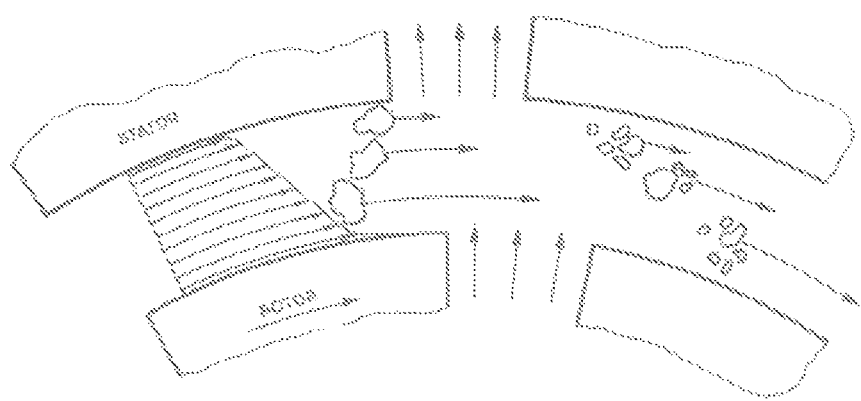

METHOD FOR TREATING BLOOD PLASMA INCLUDING A STEP OF WASHING BY MEANS OF DISPERSION

CROSS REFERENCE TO RELATED APPLICATIONS

This application claims the benefit under 35 USC 119 and/or 365 of International Application No. PCT/IB2010/055263 filed on Nov. 18, 2010 titled "METHOD FOR TREATING BLOOD PLASMA INCLUDING A STEP OF WASHING BY MEANS OF DISPERSION" and French Application No. 0958145 filed on Nov. 18, 2009 titled "PROCEDE DE TRAITEMENT DU PLASMA SANGUIN COMPRENANT UNE ETAPE DE LAVAGE PAR DISPERSION". The contents of the above-identified Applications are relied upon and incorporated herein by reference in their entirety.

TECHNICAL FIELD

The present invention relates to a method for treating blood plasma including the steps of ethanol precipitation of the plasma or a fraction of the plasma, recovering the precipitate, washing the said precipitate, recovering a washed plasma paste, and solubilizing the said washed plasma paste.

STATE OF THE ART

Fibrinogen is an essential protein for blood coagulation since its polymerization to an insoluble fibrin, formed after the cascade of reactions governing coagulation, leads to the formation of a clot which closes the vascular wound responsible for bleeding. The forming of the clot is therefore essential to stop bleeding. In addition, the fibrin formed at the wound site forms a fibrillar network which ensures tissue repair (healing).

Congenital fibrinogen deficiencies may lead to serious pathologies. To treat these deficiencies it is necessary to have fibrinogen concentrates available which can be given to patients undergoing treatment. Other pathologies may also be treated by supplies of fibrinogen, in particular in the event of massive blood loss (surgery, trauma, etc.) or subsequent to disseminated intravascular coagulation (DIC).

Also, biological glues which can be activated by fibrinogen-containing thrombin as major constituent, and Factor XIII (FXIII), are given efficient use for tissue repair in clinical use, such as skin grafts, nerve or artery sutures, as described for example in patents EP 0 305 243, FR 2 448 900 and FR 2 448 901.

The presence of Factor XIII or transglutaminase in these products contributes towards stabilizing the fibrin through the creation of intercatenary covalent bonds which make it insoluble. In some cases, these products are obtained using fairly complex methods for producing fibrinogen which require an exogenous addition of purified Factor XIII so that they may fulfil their therapeutic function.

As a result, the providing of concentrates of fibrinogen, of biological glues and of Factor XIII, in particular for therapeutic purposes, requires purification techniques leading to such products that are not only sufficiently purified of contaminants of various type e.g. accompanying or co-precipitated proteins, antibodies or proteases, but in addition are safe from a viral viewpoint.

The isolating of fractions enriched with fibrinogen, optionally containing FXIII, from plasma is known and was initially described in the work by Cohn and Nitschmann (Cohn es al., J. Am. Chem. Soc., 68, 459, 1946 and Kistler et al, Vox Sang., 7, 1962, 414-424). More recent methods combine precipitation techniques of different sources of plasma with techniques of filtration, chromatography, viral inactivation etc. For example mention may be made of the patents and patent applications EP 0 359 593, U.S. Pat. No. 5,099,003, EP 0 305 243, FR 2 448 900 and FR 2 448 901.

However, it appears that most of the methods known in the state of the art involve the use of separate production chains and hence of different methods to produce concentrates or compositions of fibrinogen, of biological glue, or enriched in fibrinogen and containing other accompanying proteins such as Factor FXIII, Factor VIII, fibronectin, von Willebrand factor etc. Most of the known methods are therefore little adapted for use on an industrial scale, in particular when there is a concomitant need for biological glue, fibrinogen and Factor XIII. The complex implementation of these purification methods on an industrial scale is further raised when the proteins of interest are intended for therapeutic use and must be subjected to inactivation and/or removal of viruses and other undesirable contaminants, e.g. prion.

Patent application EP 1 739 093 describes a single method allowing the separation of fibrinogen proteins, Factor XIII and biological glue of a solubilized plasma fraction comprising fibrinogen and Factor XIII, and leading to the preparation of lyophilized concentrates of the said proteins. The method described in application EP 1 739 093 particularly comprises the steps of chromatographic purification of a solubilized plasma fraction on an anion exchanger of weak base type under conditions allowing the retention of the biological glue, specific elution of this glue, separation of FXIII from the fibrinogen by adding at least one chemical agent precipitating FXIII, recovering the resulting solution of purified fibrinogen supernatant and diafiltration of the solutions of fibrinogen, of biological glue and of FXIII replaced in solution, followed by lyophilisation of the said solutions. The method described in patent application EP 1 739 093 may also comprise at least one viral inactivation treatment step and/or removal step of viruses and contaminants, the treatment being chosen from among chemical viral inactivation treatment, nanofiltration and dry heat treatment for viral inactivation. However, the re-suspending techniques used in the methods known in the state of the art are not fully satisfactory. Indeed, in these methods known in the state of the art, the phenomenon of shearing which occurs at the time of re-suspension may generate degradation of the proteins of interest. There is therefore a strong need for technical improvements which are able to reduce the degradation of the proteins of interest and to increase the degree of purity of the extracted proteins.

SUMMARY OF THE INVENTION

The Applicant has surprisingly discovered that the implementation of a washing step by dispersion during the preliminary preparation phase of the solubilized plasma fraction used as raw material in the method of patent application EP 1 739 093 for example, brings a significant improvement in the quality of washing compared with the methods in the state of the art which only describe a washing step by replacing in suspension. It arises therefrom that the implementing of a washing step by dispersion leads to an increase in the degree of purity of the fibrinogen in the solubilized plasma fraction, and subsequently in the concentrates of fibrinogen and biological glue resulting from implementation of the method of application EP 1 739 093 for example.

The benefits obtained with the invention are not limited to the sole method subject of application EP 1 739 093, but will be obtained with methods using the ethanol fraction (Cohn Fraction I).

The present invention therefore concerns a method for treating blood plasma comprising the steps of:
a) ethanol precipitation of the plasma or plasma fraction;
b) recovering the precipitate formed at step a);
c) washing the said precipitate by dispersion;
d) recovering a washed plasma paste; and
e) solubilizing the said washed plasma paste.

The washing by dispersion of step c) is preferably performed using a disperser of rotor/stator type, Advantageously, the disperser used is an inline disperser, the precipitate of step b) being fed to the axial inlet of the disperser and the washed product being expelled through the radial outlet of the disperser.

The method of the invention may also comprise the additional steps of:
f) treating the said solubilized plasma paste with aluminium hydroxide and/or treating the solubilized plasma paste at low temperature; and
g) obtaining a soluble plasma fraction by clarifying and/or sterilizing filtration of the supernatant resulting from step f).

The method of the invention may finally comprise the additional steps of:
h) chromatographic purification of the soluble plasma fraction of step g) on a resin of anion exchange type of weak base type, previously equilibrated with a buffer of predetermined ionic strength of basic pH, under conditions allowing the retention of the biological glue, the said biological glue being eluted by increasing the ionic strength of the said buffer;
i) precipitation of FXIII from all or part of the eluate of the biological glue obtained at step h) by adding at least one chemical agent precipitating FXIII;
j) recovering a solution of purified fibrinogen corresponding to the supernatant of step i); and
k) diafiltration of the solutions of fibrinogen and/or of biological glue and/or of FXIII replaced in solution, followed by lyophilisation of the said solutions.

Therefore, the method discovered by the Applicant, comprising the implementation of a washing step by dispersion allows the obtaining of concentrates of fibrinogen, Factor XIII and/or of biological glue that are lyophilized, highly purified, substantially free of co-purified proteins and undesirable contaminants. Indeed, the washing step by dispersion leads to a better washing of the initial plasma fraction comprising the proteins of interest, fibrinogen in particular, and leads to a significant improvement in the degree of purity of these compounds throughout the subsequent steps of the method, as compared with washing by mere replacing in suspension as described in the state of the art.

The implementation of a washing step by dispersion therefore leads to higher purity, with a simple, rapid, and low-cost method, and ensures improved cost return on the raw material (plasma or plasma fraction) on an industrial scale. It thus results a significant optimization of the production of biological glue, of Factor XIII and/or fibrinogen, whilst reducing the associated production costs.

The method of the invention further allows the Obtaining of lyophilized and highly purified proteins from a plasma raw material preferably containing fibrinogen and Factor XIII, whilst remaining compatible with at least one viral inactivation treatment and/or removal treatment of viruses and other undesirable contaminants (such as polymers, aggregates or prions).

BRIEF DESCRIPTION OF THE DRAWINGS

The single FIGURE is a schematic illustration of a rotor/stator disperser.

DETAILED DESCRIPTION OF EMBODIMENTS OF THE INVENTION

The present invention therefore concerns a method for treating blood plasma, comprising the steps of:
a) ethanol precipitation of the plasma or plasma fraction;
b) recovery of the precipitate formed at step a);
c) washing the said precipitate by dispersion;
d) recovering a washed plasma paste;
e) solubilizing the said washed plasma paste.

The method of the invention can be implemented using varied sources of plasma raw material, and in particular from sources containing fibrinogen and Factor XIII. This method can therefore be implemented directly from plasma using Cohn's fractionation method, using cold alcohol (Cohn et al, J. Am. Chem. Soc., 68, 459, 1946 and Kistler et al, Vox Sang., 7, 1962, 414-424).

Advantageously, the steps b) and d) of the method of the invention are performed by centrifugation.

In the meaning of the present invention, the term dispersion designates the separation of particles of ethanol precipitate and their homogeneous or substantially homogeneous distribution in the medium formed by the washing buffer. This dispersion differs from the re-suspending methods described in the state of the art, in particular in that these latter methods do not allow the particles to be homogeneously distributed.

In one particular embodiment, the washing step by dispersion at step c) of the method of the invention is performed using a disperser of rotor/stator type. A disperser of rotor/stator type generally comprises at least one toothed rotor and at least one toothed stator, forming an assembly with high shear speed. The product (here the ethanol precipitate mixed with the washing buffer) enters into the dispersion area between the slots of the toothed rotor and leaves via the slots of the stator ring, the pumping effect being ensured by the machine itself. The inner rotor ring increases the speed of passage of the product, the stator ring causes sudden braking thereof, promoting the fine dispersion of the product. The strong turbulences in the shear slot grind and disperse the solid particles efficiently with homogeneous distribution. The geometry of the rotor and stator can be adapted to the dispersion conditions of the product.

Said disperser is illustrated in the single FIGURE.

The disperser, in particular an inline rotor/stator disperser, therefore allows a homogeneous or substantially homogeneous solution to be obtained, with a very fine, homogeneous or substantially homogeneous dispersion of the ethanol precipitate in the washing buffer, and thereby contributes to the removal of a greater proportion of protein contaminants.

While the use of rotor/stator type dispersers is known in the state of the art for preparing emulsions, suspending pigments, incorporating detergents in a solution, for rapid manufacturing of colloid solutions and for homogenizing powders and other similar products, it is to be noted that the use of said dispersers is not described with respect to purification methods of plasma proteins.

It is effectively known that the use of a disperser causes heating of the solution or of the prepared suspension, and that a said disperser cannot be used in a thermostat-controlled tank. It therefore appeared probable, on the date of the present invention, to consider that the use of a disperser in methods for preparing plasma products would lead to an increase in temperature, thereby causing the degradation of the plasma proteins.

Yet, the Applicant has surprisingly observed that the use of a disperser reduces the time needed for dispersion and in fact reduces the heating thereof. Therefore contrary to current technical preconceived opinion, and surprisingly, the use of a disperser proves to be particularly suited to a method for purifying plasma proteins insofar as it does not generate any degradation of the product.

In addition, the applicant has also observed that the use of a disperser leads to a significant decrease in the quantity of contaminating proteins.

In one preferred embodiment, the washing step by dispersion of step c) of the method of the invention is performed using an inline disperser. In this particular case, the disperser preferably of rotor/stator type is mounted on the same production line as the other industrial elements required for implementing the purification method. The precipitate of step b) is therefore fed, preferably with the washing buffer, to the axial inlet of the inline disperser, and the washed product corresponding to a substantially homogeneous dispersion of the ethanol precipitate in the washing buffer is expelled towards the radial outlet of the inline disperser.

The use of an inline disperser further offers every guarantee of asepsis since the machine is designed for simple dismounting and easy cleaning and can be integrated in a CIP system (Clean-In-Place).

As discussed above, the washing of the ethanol precipitate using a disperser at step c) of the method of the invention leads to obtaining a homogeneous or substantially homogeneous suspension (a homogenate) of the ethanol precipitate in the washing buffer used. This homogeneous or substantially homogeneous suspension can be characterized by a visual control allowing verification of the absence of agglomerate in the suspension.

In one particular embodiment, step c) of the present invention is performed using a tank equipped with an stirring means of deflocculating blade type. This stirring means allows to form the primary dispersion, which leads to a deflocculated paste but which is non homogeneous. The stirring means is coupled with an inline disperser system, which allows to form the secondary dispersion leading to fine and homogeneous suspension.

In one preferred embodiment, the recovery of the precipitate performed at step b) and/or the recovery of the plasma paste at step d) are carried out by centrifugation. Preferably, the recovery of the plasma paste at step d) is obtained by using an injection centrifuge. In this particular case, the precipitate washed by dispersion at step e) is placed in an industrial centrifuge by means of injectors whose diameter is calibrated in relation to the size of the particles in suspension. In one preferred embodiment, the injection centrifuge is of <<Sharpless AS 16>> type or <<Westfalia Separator>> type, having specific injectors calibrated in relation to the separator used (2 to 4 mm).

Washing by dispersion at step c) allows the obtaining of a suspension comprising very fine particles of ethanol precipitate in the washing buffer. It results that, the substantially homogeneous suspension formed proves to be particularly suited to the use of an injector centrifuge insofar as it advantageously prevents clogging of the centrifuge injectors.

In one preferred embodiment, the solubilizing of the plasma paste is performed in a buffer containing 0.06-0.18 M sodium chloride, 0.005-0.02 M trisodium citrate and 0.02-0.08 M arginine, at pH 7.3 to 7.5.

In one preferred embodiment, the precipitate formed by ethanol precipitation is washed by dispersion with a buffer consisting of a mixture of 0.5-1.5 M glycine, 0.01-0.1 M trisodium citrate and 5.0-8.0% (v/v) ethanol, at pH 6.7-6.9.

In one preferred embodiment, the method of the invention comprises the additional steps of:
f) treating the said solubilized plasma paste with aluminium hydroxide and/or treating the said solubilized plasma paste at low temperature;
g) obtaining a soluble plasma fraction by clarifying and/or sterilizing filtration of the supernatant resulting from step f).

The adding of aluminium hydroxide at step f) particularly ensures the elimination of undesirable proteins such as Factors II (FII), VII (FVII), IX (FIX) and X (FX). The supernatant resulting from the treatment of the solubilized plasma paste, also designated the <<soluble plasma fraction>> in the present application, is purified by at least one clarifying and/or sterilizing filtration. The soluble plasma fraction can also undergo depth filtration for the purpose of allowing the retention of aluminium hydroxide.

Clarifying filtration allows the removal of insoluble contaminating particles. The clarifying and sterilizing filtrations are generally performed using filters from 0.8 to 0.1 µm for example. At least one clarifying filtration is advantageously performed in the form of filtration on 0.65 µm filters in cellulose fibres. In one preferred embodiment, at least one sterilizing filtration is performed using 0.2 µm filters.

The soluble plasma fraction obtained after step g) can be used directly or, when necessary it can be frozen until the implementation of optional, additional purification steps.

The implementation of the method for treating blood plasma comprising a washing step by dispersion advantageously allows a degree of fibrinogen purity in the soluble plasma fraction to be obtained of at least 80 preferably at least 85%, more preferably at least 90%.

The use of an inline dispersion system during the washing step particularly improves the enriching with fibrinogen at the soluble plasma fraction stage. This technology allows to obtain conforming and reproducible results in terms of homogeneity of the suspension at the time of inline dispersion and of fibrinogen enrichment at the washing step, and hence in the subsequent steps without the protein of interest undergoing any degradation.

In one preferred embodiment, the method for treating blood plasma according to the invention comprises the additional steps of:
h) chromatographic purification of the soluble plasma fraction at step g) on a resin of anion exchange type of weak base type previously equilibrated with a buffer of predetermined ionic strength and of basic pH, under conditions allowing the retention of the biological glue, the said biological glue being eluted by increasing the ionic strength of the said buffer;
i) precipitation of TAM from all or part of the ciliate of biological glue by adding at least one chemical agent precipitating FXIII;
j) recovery of a purified fibrinogen solution corresponding to the supernatant at step i); and k) diafiltration of the solutions of fibrinogen and/or of the biological glue and/or of FXIII replaced in solution, followed by lyophilisation of the said solutions.

The chromatographic purification of the soluble plasma fraction (step h)) can be performed on any matrix based on a natural or synthetic polymer, a resin or gel on which anion exchange groups of weak base type are grafted, such as DEAE. The conventional chromatographic supports of this type are available under the names DEAE-Sepharose CL-6B, DEAE-Trisacryl LS, Fractogel TSK-DEAE 650 M or S, DEAE-Macroprep (Bio-Rad, France) etc.

The equilibration buffer of the anion exchanger has a predetermined ionic strength and must have basic pH. The ionic strength is typically less than the value of 0.2 and preferably it lies in the range of values from 0.06 to 0.2, in particular from 0.08 to 0.15.

This is preferably adjusted through the addition of inorganic salts of alkaline or alkaline-earth metals, or a mixture thereof, in most preferred manner inorganic salts of alkaline metals and in particular sodium chloride.

The maximum pH value of the equilibration buffer is chosen so as to avoid any denaturing of the products under consideration, namely it is about 10.

Advantageously, the pH lies in the range of values higher than 7 and up to 9, preferably from 7.5 to 8.2

As an example, this buffer is composed of sodium chloride at a pH of 7.9-8.1, having a concentration of 0.06 M, and may most preferably also comprise trisodium citrate at a preferred concentration of 0.011 M. It is also possible to use any other buffer based on sodium chloride or inorganic salts of alkaline or alkaline-earth metals and comprising other biologically compatible compounds that are non-denaturing for the products of interest.

When the soluble plasma fraction has been applied to the anion exchanger, the operating conditions are such that the biological glue is retained on the support.

In one preferred embodiment, prior to the elution step of the biological glue, the method of the invention may comprise a washing step of the anion exchanger using the said equilibration buffer until removal of the proteins and non-retained contaminants. This washing step, via percolation of the washing buffer on the support, allows the passing into the filtrate of proteins present in the fibrinogen-containing solution such as the immunoglobulins G (IgG), A (IgA) and M (IgM) and albumin, and the contaminants not or only weakly retained by the exchanger such as the chemical viral inactivation agents. The washing time is determined by measuring the optical density (OD) of the filtrate at the wavelength of 280 nm indeed, an OD value corresponding to that of the baseline is a good indication of the effective removal of the above-cited compounds.

In one preferred embodiment, the washing buffer used corresponds to the equilibration buffer of the column and is preferably formed of 0.02-0.1 M sodium chloride and 0.005-0.02 M trisodium citrate, at pH 7.8-8.2.

After return to baseline, the elution of the biological glue is performed by increasing the ionic strength of the equilibration or washing buffer whose OH is preferably set at 7.4-7.6. The value of this ionic strength is chosen so as to obtain efficient elution of the biological glue whilst taking care that this value does not deteriorate the properties of the product under consideration.

Advantageously, the value of the ionic strength of the elution buffer is between 0.5 and 1.3, in particular between 0.9 and 1.1. This increase in ionic strength is obtained by adding any salt or mixture of salts defined above, sodium chloride in particular. The elution buffer may also contain other excipients such as a mixture of constituents called mixture A comprising trisodium citrate (10 to 12 g/l), lysine (1 to 5 g/l), glycine (1 to 5 g/l), Tris salt (2 to 5 g/l), arginine (25 to 50 g/D and isoleucine (5 to 15 g/l).

The protein concentration in the eluate is generally of the order of 4 g/l.

At least part of the harvested quantity of biological glue eluate can then be y d to a treatment intended to separate the FXIII accompanying the fibrinogen.

This separation is performed by causing the precipitation of FXIII through the addition to the eluate of step h) of a precipitating chemical agent, possibly in the form of an aqueous solution at an appropriate concentration to obtain precipitation of Factor XIII.

Preferably, the precipitating chemical agent is an aqueous solution containing 1 M citrate salts such as sodium citrate, and in particular trisodium citrate.

The formed precipitate of FXIII is then separated from the supernatant highly enriched with fibrinogen.

In one preferred embodiment, the precipitate of FXIII can be recovered by filtration through 5 µm filters.

The precipitate of FXIII thus recovered is then replaced in solution, preferably in water or a buffer. In one preferred embodiment, the precipitate of FXIII is dissolved in a buffer comprising a mixture of 10 to 12 trisodium citrate, 1 to 5 g/l lysine, 1 to 5 g/l glycine, 2 to 5 g/l Tris, 25 to 50 g/l arginine and 5 to 15 g/l isoleucine, adjusted to a pH comprises between 6.9 and 7.1, so that the concentration of Factor XIII corresponds to an activity about 100 times greater than that of normal plasma.

In this respect, the precipitate of FXIII can be dissolved for example so that it has a concentration of about 1 to 5 g whole proteins/l.

According to the invention, the solutions of biological glue (i.e. the eluate of biological glue resulting from step h)) and of fibrinogen (supernatant enriched with fibrinogen) can advantageously be concentrated by ultrafiltration, up to contents typically comprise between 15 and 25 g whole proteins/l, determined using conventional measurements known to persons skilled in the art.

The three solutions of fibrinogen, of Factor XIII and of biological glue that are obtained, optionally concentrated, are then subjected to a diafiltration step.

The diafiltration step allows the removal of any excess inorganic salt used to obtain solutions having an ionic strength of no more than 0.2M, and of precipitating agent present in the precipitate replaced in solution. It is to be noted that a large presence of inorganic salt, needed for elution of the biological glue, could have a harmful influence on the efficacy of the process of lyophilisation and viral inactivation by dry heating as well as on the virus-retaining capacity of a suitable nanofilter.

The diafiltration step can also be used to incorporate adequate excipients such as stabilizers and/or protectors intended on the one hand to allow dry heating of the fibrinogen, of FXIII and of biological glue without risk of denaturing, and on the other hand to allow rapid solubilizing of the lyophilisates typically in 3 to 8 min.

In one preferred embodiment, the diafiltration buffer containing mixture A (comprising a mixture of 10 to 12 g/l trisodium citrate, 1 to 5 gill lysine, 1 to 5 glycine, 2 to 5 g/l Tris, 25 to 50 g/l arginine and 5 to 15 g/l isoleucine) and has a pH of 6.9-7.1.

Advantageously, the diafiltration buffer comprising the mixture A is the same as the one used to elute the biological glue from the anion exchange resin. In this preferred embodiment, the implementing of diafiltration and of the method of the invention are thereby simplified and optimized.

Diafiltration buffers of different composition can also be used in relation to needs, provided that they meet the criteria set forth above. The ultrafiltration step mentioned above can also be implemented under the same conditions at this stage of the method.

The diafiltered solutions optionally concentrated by ultrafiltration, are lyophilized following conventional methods and usual conditions, namely between −40° C. and −30° C. for about 48 hours.

In one preferred embodiment, the method of the invention comprises at least one viral inactivation and/or removal treatment of viruses and contaminants step such as the prion for example. This treatment can be chosen from the group formed by chemical viral inactivation treatment, nanofiltration and dry heat viral inactivation.

When the viral inactivation treatment is a chemical treatment, it advantageously corresponds to solvent-detergent treatment, following the method described in patent EP 0 131 740. The viral inactivation chemical agents used preferably correspond to a mixture of Tween-TnBP, and more preferably to a mixture of Triton (octoxinol)-TnBP, whose typical concentrations are respectively 0.3% (v/v) and 1% (w/v). Viral inactivation by chemical treatment can be integrated at any stage of the method, but it is judiciously performed before the chromatographic purification of step h). In this manner, chromatographic purification will contribute to the efficient removal of inactivation agents.

In one preferred embodiment of the method, provision may also be made for nanofiltration step to remove viruses, in particular non-enveloped viruses, and other exogenous contaminants, the said step possibly being used in addition to the chemical viral inactivation treatment described above. Nanofiltration can advantageously be performed on filters having a porosity of 35 nm and/or 15 nm, although other nanometric filters can be used insofar as the filtration times and efficacy of viral retention are optimized.

Nanofiltration is advantageously performed either on the eluate resulting from step h) or, when applicable, on the diafiltered solutions of fibrinogen, of biological glue and/or of FXIII replaced in solution, before lyophilisation thereof.

It is to be noted that the technique of nanofiltration, for efficient implementation, requires control over the physico-chemical parameters influencing the yield of recovered compounds to be filtered, while avoiding clogging of the filter and the passing of various viruses and contaminants. These parameters, such as ionic strength, pH of the solution, and the filtration operating conditions, impose specific implementation conditions which also depend on the type of the compound(s) present in the solution to be filtered.

The judicious choice of chemical parameters for chromatographic purification and those of diafiltration therefore allows nanofiltration to be performed without deteriorating performance level.

Finally, a dry heat viral inactivation treatment is advantageously performed on the lyophilisates of fibrinogen, biological glue and FXIII obtained after the lyophilisation step, using conventional conditions of 80° C. for 72 hours to inactivate the non-enveloped, viruses which may not have been inactivated and/or removed by at least one of the two steps of viral inactivation and/or viral removal described above.

The dry-heated lyophilisates can then be reconstituted in an aqueous medium compatible with clinical use, preferably in purified water for injection (WFI) and directly injected via intravenous route.

Therefore, the implementing of the method leads to lyophilisates of highly purified concentrates of biological glue and of fibrinogen, whose respective fibrinogen content relative to the total protein content is about 85 to 90%.

Without the use of the inline disperser, the fibrinogen content relative to the total protein content is between 70 and 77% (see Table A).

In addition, the activities of Factor XIII in the concentrates of biological glue and fibrinogen are respectively about 5 U/ml and about 1.5 U/ml.

The concentrate of Factor XIII obtained is free of contaminating proteins and has an activity, according to needs, in the range of values from about 30 U/ml to about 700 U/ml, preferably from 100 U/ml to 400 U/ml, obtained according to the concentration of FXIII precipitate replaced in solution and/or the concentration obtained after ultrafiltration.

In addition, the presence of at least one viral inactivation treatment step and/or removal step of viruses and contaminants in the method of the invention makes that the concentrates of biological glue, fibrinogen and Factor XIII able to be obtained with this method suitable for therapeutic use.

The following example illustrates one embodiment of the present invention without limiting the scope thereof however.

EXAMPLE 1200 l of human plasma free of cryoprecipitate are used. This plasma is subjected to ethanol precipitation following Cohn's method, under conditions known to persons skilled in the art, such that the concentration of ethanol in the plasma under consideration is 8% (v/v) and the temperature of the mixture thus obtained is −3° C. to −5° C.

The supernatant and the precipitate thus obtained are then centrifuged. Between 8 and 12 kg of ethanol precipitate is obtained, which forms Cohn impure Fraction I.

Cohn's impure Fraction I is re-suspended and washed with 300 l of <<Blombach>> buffer (Blombäck B, Blombäck M: Purification of human and bovine fibrinogen. Ark Kern 10:415-443, 1956) formed of a mixture of 1 M glycine, 0.055 M tridosium citrate and 6.5% ethanol (v/v), at a pH of 6.8.

The washing is performed using an inline dispersion system of type Z66 (Ystral).

After centrifugation on Sharpless AS 16 centrifuge, with injectors calibrated at 3 mm, about 8 kg of washed plasma paste are recovered (Cohn purified Fraction I) which are dissolved at a temperature of 37° C., in 60 l of buffer formed of a mixture of 0.12 M sodium chloride, 0.010 M trisodium citrate and 0.05 M arginine, at pH 7.4.

The solubilized plasma paste thus obtained is then subjected to treatment with alumina gel to the rate of 108 g per 1 kg of plasma paste, at a temperature of 25° C. and a pH of 6.9-7.1. Once the treatment with alumina gel is completed, the solution is subjected to depth lenticular filtrations using filters in cellulose fibres (Seitz, type K700) of 0.65 µm and sterilizing filtrations using 0.2 µm filters.

This solution is then subjected to a first viral inactivation treatment by solvent-detergent in the presence of Tween-TnBP, of respective concentrations of 0.3% (v/v) and 1% (w/v), according to the method described in EP 0 131 740.

Table A compares the concentration of fibrinogen, of proteins and the degree of purity of the fibrinogen obtained when implementing a method comprising a washing step by inline dispersion (such as described above) with those of a similar method in which the washing step is performed in the absence of an inline dispersion system.

It is to be noted that the results given in Table A correspond to mean values respectively obtained from 2 different batches of plasma for the method not comprising any washing step by dispersion and from 3 different plasma batches for the method which does comprise a washing step by dispersion. With the exception of the use of an inline disperser of rotor/stator type when washing the ethanol precipitate, the methods described in Table A are strictly comparable (including for all the buffers and temperatures used).

TABLE A

Results of controls during production

| | | Method not comprising a washing step by dispersion Mean of 2 batches | Method comprising a washing step by inline dispersion Mean of 3 batches |
|---|---|---|---|
| Raw plasma material before ethanol precipitation | Volume (L) | 796 | 778 |
| | Proteins (g/L) | 56 | 54.83 |
| | Coagulable fibrinogen (g/L) | 1.55 | 1.46 |
| | Fibrinogen purity (%) | 2.76 | 2.66 |
| Solubilized plasma paste | Volume (L) | 53 | 54.33 |
| | Proteins (g/L) | 21.25 | 17.83 |
| | Coagulable fibrinogen (g/L) | 15.15 | 15.9 |
| | Fibrinogen purity (%) | 71.29 | 89.17 |
| Supernatant obtained after treatment of the solubilized plasma paste with aluminium hydroxide | Volume (L) | 55 | 54 |
| | Proteins (g/L) | 16.5 | 15.16 |
| | Coagulable fibrinogen (g/L) | 11.85 | 12.96 |
| | Fibrinogen purity (%) | 71.81 | 85.13 |
| Soluble plasma fraction after clarifying and sterilizing filtration | Volume (L) | 53.45 | 53.3 |
| | Proteins (g/L) | 16 | 14.33 |
| | Coagulable fibrinogen (g/L) | 12.35 | 12.53 |
| | Fibrinogen purity (%) | 77.18 | 87.43 |

It is clearly apparent that the results obtained with the inline disperser are significantly higher insofar as the degree of purity of the fibrinogen is always significantly higher than the purity obtained with the method using a conventional washing system. It therefore appears that the efficacy of the inline disperser that was used contributed to the improvement of the washing step and hence to the increase in fibrinogen purity at this stage of the method. The inline disperser therefore allows a more homogeneous solution to be obtained, with a very fine dispersion of the ethanol precipitate in the washing buffer, and on this account contributes to the removal of a greater proportion of contaminants. It is further important to note that visual control of the solution does not evidence any agglomerates which might clog the centrifuge injectors in the steps following after the washing step.

In addition, the concentrations of different contaminating proteins were measured in the soluble plasma fraction resulting from this first part of the method. These results are summarized in Table B below:

TABLE B

| | | Method not comprising any washing step by dispersion Mean of 2 batches | Method comprising a washing step by inline dispersion Mean of 3 batches |
|---|---|---|---|
| Whole proteins Co-purified proteins | g/L | 16.00 | 14.33 |
| Fibronectin | mg/L | 746.75 | 607.8 |
| IgG | mg/L | 837.25 | 325.5 |
| IgA | mg/L | 92.35 | 83.81 |
| IgM | mg/L | 257.75 | 114.9 |
| C3c | g/L | 0.13 | 0.06 |
| C4 | g/L | 0.155 | 0.036 |
| Plasminogen | µg/L | 69.68 | 53.25 |

TABLE B-continued

| | | Method not comprising any washing step by dispersion Mean of 2 batches | Method comprising a washing step by inline dispersion Mean of 3 batches |
|---|---|---|---|
| FII | µU/L | 743.8 | 578.1 |
| Co-purified proteins | g/L | 2.362 | 1.289 |
| Co-purified proteins | % | 14.76 | 8.99 |

It is clear from the results given in Table B that the washing step by inline dispersion allows the removal of a significantly higher number of co-purified proteins (contaminating proteins) accompanying the fibrinogen.

The diluted soluble plasma fraction is then injected into a chromatography column filled with Macropep DEAE anion exchange gel (Bio-Rad, France), previously equilibrated with buffer formed of 0.06 M sodium chloride and 0.011 M trisodium citrate, adjusted to a pH of 8.0 M, of osmolality 130-150 mosmolkg$^{-1}$. Under these conditions, the fibrinogen and Factor XIII, forming the biological glue, are retained by the support. The proteins weakly or not retained on the support are removed in the filtrate, as well as the Tween and TnBP, by several successive washings with the same buffer.

When the OD, measured at 280 nm, has fallen to the value of the baseline value, the elution of the fibrinogen and Factor XIII, forming the biological glue, is performed with an elution buffer containing 1M sodium chloride and a mixture A' formed of trisodium citrate (11.2 g/l), lysine (2.0 g/l), glycine (2.0 g/l), Tris salt (2.40 g/l), arginine (40 g/l) and isoleucine (10 g/l), adjusted to a pH of 7.5, of osmolality>2000 mosmolkg$^{-1}$.

The eluate of purified biological glue thus recovered is subjected to nanofiltration on PLANOVA filters (Asahi—Japan) of 35 nm and surface area of 1 m$^2$, in order to remove the viruses which might not have been inactivated by the above solvent-detergent treatment. The content of whole proteins at this stage of the method is about 4.0 g/l of solution.

50% of the volume of the biological glue eluate is isolated and a 1M trisodium citrate solution is added to the remainder of the volume of the ciliate to precipitate Factor XIII. After ensuring that all the Factor XIII has been precipitated, the precipitate is isolated and recovered by filtration on 5 μm Sartopure filters (Sartorius—France).

The FXIII precipitate thus recovered is replaced in solution in purified water for injection to the proportion of about 1 g/l.

The solutions of biological glue (eluate) and fibrinogen are concentrated by ultrafiltration on Biomax Millipore 100 kDa filters of 5 m$^2$ surface area, so that the protein content of each of the solutions reaches 15 g/l.

The above concentrated solutions and the FXIII solution are subjected to diafiltration, on the same filters as those used for ultrafiltration, against mixture A defined above of pH 6.9-7.1, osmolality of 590-610 mosmolkg$^{-1}$, which also allows the removal of sodium chloride.

After performing sterilizing filtration on filters of 0.45-0.2 μm, 100 ml of the respective diafiltered solutions are sampled and placed in glass bottles for lyophilisation performed at between −40° C. and −30° C. for about 48 hours.

The lyophilisates of fibrinogen, of biological glue and Factor XIII obtained are subjected to a final viral inactivation step by dry heating to 80° C. for 72 hours and stored until subsequent therapeutic use.

What is claimed is:

1. A method for treating blood plasma comprising the steps of:
   a) ethanol precipitation of the plasma or a fraction of the plasma to form a precipitate;
   b) recovering the precipitate formed at step a);
   c) washing the said precipitate by dispersion using a disperser of rotor/stator type;
   d) recovering a washed plasma paste; and
   e) solubilizing the said washed plasma paste.

2. The method for treating blood plasma according to claim 1, wherein the washing by dispersion of step c) is performed using an inline disperser, the precipitate of step b) being fed to the axial inlet of the disperser and the washed product being expelled at the radial outlet of the disperser.

3. The method for treating blood plasma according to claim 1, wherein at least one of the recovery of the precipitate at step b) and the recovery of the plasma paste at step d) are carried out by centrifugation.

4. The method for treating blood plasma according to claim 3, wherein the recovery of the plasma paste at step d) is carried out using an injection centrifuge.

5. The method for treating blood plasma according to claim 1, wherein the product washed at step c) is substantially homogeneous.

6. The method for treating blood plasma according to claim 1, comprising the additional steps of:
   f) treating the said solubilized plasma paste with aluminium hydroxide and/or treating the said solubilized plasma paste at low temperature;
   g) obtaining a soluble plasma fraction by clarifying and/or sterilizing filtration of the supernatant resulting from step f).

7. The method for treating blood plasma according to claim 1, wherein the washing by dispersion of step c) is performed with a buffer consisting of a mixture of 0.5-1.5 M glycine, 0.01-0.1 M trisodium citrate and 5.0-8.0% (v/v) ethanol at a pH of 6.7-6.9.

8. The method for treating blood plasma according to claim 6, comprising the additional steps of:
   h) chromatographic purification of the soluble plasma fraction of step g) on a resin of anion exchange type of weak base type previously equilibrated with a buffer of predetermined ionic strength of basic pH, under conditions allowing the retention of the biological glue, the said biological glue being eluted by increasing the ionic strength of the said buffer;
   i) precipitation of FXIII from all or part of the biological glue eluate obtained at step h) by adding at least one chemical agent precipitating FXIII;
   j) recovery of a purified fibrinogen solution corresponding to the supernatant of step i); and
   k) diafiltration of the solutions of fibrinogen and/or of biological glue and/or of FXIII replaced in solution, followed by lyophilisation of the said solutions.

9. The method according to claim 1, wherein said method comprises at least a viral inactivation treatment step and/or removal step of viruses and contaminants, the treatment being chosen from the group formed by chemical viral inactivation treatment, nanofiltration and viral inactivation treatment by dry heating.

10. The method according to claim 8, wherein said method comprises a concentrating ultrafiltration step performed prior to the diafiltration step k) or after the diafiltration step k), but before lyophilisation.

11. A method of treating blood plasma comprising the steps of:
   ethanol precipitation of the plasma or a fraction of the plasma to form a precipitate;
   recovering the precipitate formed;
   separating particles of ethanol precipitate from one another using a disperser of rotor/stator type;
   homogeneously distributing the particles;
   suspending the particles to form a washed plasma paste;
   recovering the paste; and
   solubilizing the paste.

* * * * *